(12) United States Patent
Dayioglu

(10) Patent No.: US 12,409,281 B2
(45) Date of Patent: Sep. 9, 2025

(54) METHOD OF ASSEMBLY OF INHALER ARTICLE HOLDER

(71) Applicant: PHILIP MORRIS PRODUCTS S.A., Neuchâtel (CH)

(72) Inventor: Onur Dayioglu, Neuchâtel (CH)

(73) Assignee: Philip Morris Products S.A., Neuchâtel (CH)

( * ) Notice: Subject to any disclaimer, the term of this patent is extended or adjusted under 35 U.S.C. 154(b) by 214 days.

(21) Appl. No.: 18/265,582

(22) PCT Filed: Dec. 9, 2021

(86) PCT No.: PCT/IB2021/061518
§ 371 (c)(1),
(2) Date: Jun. 6, 2023

(87) PCT Pub. No.: WO2022/123487
PCT Pub. Date: Jun. 16, 2022

(65) Prior Publication Data
US 2024/0033451 A1    Feb. 1, 2024

(30) Foreign Application Priority Data
Dec. 11, 2020 (EP) .................................... 20213340

(51) Int. Cl.
*A61M 15/00* (2006.01)

(52) U.S. Cl.
CPC ........ *A61M 15/004* (2014.02); *A61M 15/003* (2014.02); *A61M 2202/064* (2013.01); *A61M 2207/00* (2013.01)

(58) Field of Classification Search
CPC ............ A61M 15/003; A61M 2207/00; A61M 2205/583
See application file for complete search history.

(56) References Cited

U.S. PATENT DOCUMENTS

2011/0277752 A1    11/2011   Cheu et al.

FOREIGN PATENT DOCUMENTS

EP        3 481 471 A1     5/2019
WO    WO-2013115184 A1 *  8/2013  ............... B21G 1/08
(Continued)

OTHER PUBLICATIONS

European Search Report for EP 20213340.1 issued by the European Patent Office on Jun. 14, 2021; 8 pgs.
(Continued)

*Primary Examiner* — Daniel McNally
(74) *Attorney, Agent, or Firm* — Mueting Raasch Group

(57) ABSTRACT

A method of assembling an inhaler article holder having an oriented piercing element, includes inserting an inner housing into a jig. The inner housing extends along a longitudinal axis from a proximal end to a distal end an inner housing length. The distal end includes a piercing element aperture. The inner housing length mates with a jig opening. The jig includes a jig angled planar surface coaxial with the piercing element aperture. The method includes mating a piercing element cutting plane with the jig angled planar surface. The piercing element extends from a proximal cutting end to the piercing element distal end defining a cutting plane. The piercing element distal end is received in the inner housing piercing element aperture, and then fixing the piercing element distal end to the inner housing. The piercing element cutting plane is orientated relative to the inner housing longitudinal axis.

19 Claims, 11 Drawing Sheets

(56) References Cited

FOREIGN PATENT DOCUMENTS

WO     WO 2019/159123 A1     8/2019
WO     WO-2020178715 A1 *     9/2020     ............. A24F 13/08

OTHER PUBLICATIONS

International Search Report and Written Opinion for PCT/IB2021/061518, issued by the European Patent Office on Feb. 23, 2022; 11 pgs.

Marple et al., "Next generation pharmaceutical impactor (a new impactor for pharmaceutical inhaler testing). Part I: Design," *Journal of Aerosol Medicine*, 2003;16(3):283-99.

Marple et al., "Next generation pharmaceutical impactor (a new impactor for pharmaceutical inhaler testing). Part II: Archival calibration," *Journal of Aerosol Medicine*, 2003;16(3):301-324.

* cited by examiner

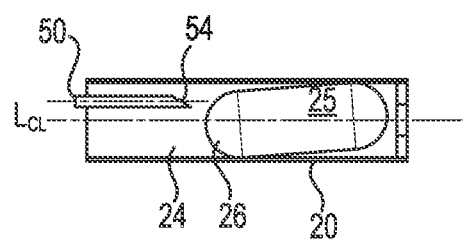
FIG. 8
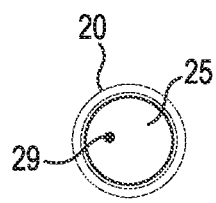 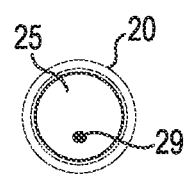
FIG. 9A  FIG. 9B

METHOD OF ASSEMBLY OF INHALER ARTICLE HOLDER

This application is the § 371 U.S. National Stage of International Application No. PCT/IB221/061518, filed 9 Dec. 2021, which claims the benefit of European Application No. 20213340.1, filed 11 Dec. 2020, the disclosures of which are incorporated herein by reference.

The present invention related to methods of assembly of an inhaler article holder. Specifically, the inhaler article holder includes a single offset piercing element with a specific orientation.

Dry powder inhalers are not always fully suitable to provide dry powder particles to the lungs at inhalation or air flow rates that are within conventional smoking regime inhalation or air flow rates. Dry powder inhalers may be complex to operate or may involve moving parts. Dry powder inhalers often strive to provide an entire dry powder dose or capsule load in a single breath.

Inhaler articles may retain capsules containing dry powder. These capsules may be activated by piercing an aperture though the capsule wall with a piercing element. A user then puffs (draws or inhales) from the consumable mouthpiece side. This action forces air flow through the dry powder inhaler.

Activating the dry powder capsule requires piercing the capsule to form an aperture. Dry powder particles then may exit the capsule through the aperture during inhalation and consumption of the dry powder particles by entraining the dry particles in the inhalation air flow to the consumer. Forming a reliable open aperture on the capsule hemispherical end has proven to be difficult. The aperture tends to reclose once the piercing element is withdrawn from the capsule. In addition, the piercing element tends to strike the capsule hemispherical end at different locations leading to non-uniform shaped apertures. This leads to unpredictable and variable dry powder delivery to the consumer.

It is desirable to assemble an inhaler system or inhaler article holder that ensures reliable placement and orientation of a single cutting plane within the device. It is desirable to assemble such inhaler system or inhaler article holder with a simple and reliable method. Such methods would provide an inhaler system that reliably pierces the capsule to form a uniform single stable aperture and provide predictable and uniform dry powder delivery to the user over a multitude of inhalations.

According to an aspect of the present invention, there is provided a method of assembling an inhaler article holder having an oriented piercing element, comprising, inserting an inner housing into a jig. The inner housing extends along a longitudinal axis from a proximal end to a distal end an inner housing length. The distal end comprising a piercing element aperture. The inner housing length mates with a jig opening. The jig comprising a jig angled planar surface coaxial with the piercing element aperture. The method includes mating a piercing element cutting plane with the jig angled planar surface. The piercing element extending from a proximal cutting end along a piercing element longitudinal axis to the piercing element distal end. The piercing element cutting plane defines the piercing element proximal cutting end. The piercing element distal end is received in the inner housing piercing element aperture, and then fixing the piercing element distal end to the inner housing. Wherein the piercing element cutting plane is orientated relative to the inner housing longitudinal axis.

According to an aspect of the present invention, there is provided a method of assembling an inhaler article holder having an oriented piercing element, comprising, inserting an inner housing into a jig. The inner housing extends along a longitudinal axis from a proximal end to a distal end an inner housing length. The distal end comprising a piercing element aperture. The inner housing length mates with a jig opening. The jig comprising a jig angled planar surface coaxial with the piercing element aperture. The method includes mating a piercing element cutting plane with the jig angled planar surface. The piercing element extending from a proximal cutting end along a piercing element longitudinal axis to the piercing element distal end. The piercing element cutting plane defines the piercing element proximal cutting end. The piercing element distal end is received in the inner housing piercing element aperture, and then fixing the piercing element distal end to the inner housing. Wherein the piercing element cutting plane is orientated relative to the inner housing longitudinal axis. The piercing element is parallel with but offset from the longitudinal axis of the inhaler device or capsule cavity.

The term "jig" refers to frame element for holding and aligning work pieces for assembly.

Some inhaler systems that utilize a single piercing element to pierce a capsule place this single piercing element co-incident with a central longitudinal axis of the device or capsule cavity so that the piercing element strikes the capsule at the central axis of the capsule. It is expected that this configuration would provide a balanced piercing force onto the capsule and avoid a bending moment on the piercing element or the capsule during activation of the capsule.

Applicant has discovered that placing the single piercing element parallel with but offset from the longitudinal axis of the inhaler device or capsule cavity, improves the quality and reliability of the aperture formed in the capsule hemispherical end by the offset piercing element. Specifically, when this single offset piercing element starts cutting on a surface closer to the piercing element (along the hemispherical surface of the capsule endcap) to a surface further away from the initial cut point, a hinge of capsule material is formed on the portion forming the apertures perimeter that is furthest from the initial cut point. This specific orientation of the piercing element cutting plane produces a stable open aperture as compared to any other orientation of this piercing element cutting plane.

Assembling an inhaler system or inhaler article holder that ensures reliable placement and orientation of a single cutting place piercing element within the device is difficult. Applicant has discovered the utilizing a jig to orient and place the offset piercing element cutting plane relative to the inner housing advantageously provides a simple and reliable method to assemble an inhaler system or inhaler article holder having the desired piercing element orientation. The single offset piercing element is relatively easy to assembly into an inhaler article holder utilizing the jig described herein. The inhaler article holder single offset piercing element provides predictable improved uniform dosing over a multitude of inhalations.

This disclosure is directed to a holder for an inhaler article, referred to as an "inhaler article holder". The inhaler article holder includes a single offset piercing element. The inhaler article holder is configured to receive a consumable inhaler article, activate the capsule within the inhaler article by piercing the capsule, and induce swirling inhalation airflow into an inhaler article during consumption. The inhaler article holder and an inhaler article may form an inhaler system to which this disclosure is directed.

The inhaler article holder described herein may be combined with an inhaler article containing a capsule. The inhaler article may be used to activate the inhaler article by piercing the capsule, providing reliable activation of the capsule by puncturing the capsule with the piercing element of the inhaler article holder. Particles may be released from the capsule upon drawing or creating an airflow around the pierced capsule. The inhaler system thus delivers the dry powder particles to a consumer. The inhaler article holder is separate from the inhaler article, but the consumer utilizes both the inhaler article and the inhaler article holder while consuming the dry powder particles released within the inhaler article. A plurality of these inhaler articles may be combined with an inhaler article holder to form a system or kit. A single inhaler article holder may be utilized on 10 or more, or 25 or more, or 50 or more, or 100 or more, inhaler articles to activate (puncture or pierce) a capsule contained within each inhaler article and provide reliable activation. The inhaler article may optionally provide a visual indication (marking), for each inhaler article of the activation of the inhaler article.

The inhaler article has an airflow path. Airflow is introduced into the inhaler article by an inhalation (or puff) from a user. The inhaler article holder creates swirling inhalation airflow. This swirling inhalation airflow is introduced to the inhaler article. The distal end or upstream-most end of the inhaler article includes an open aperture that defines an open central passage of the open tubular element configured to receive swirling inhalation airflow.

The swirling inhalation airflow then continues downstream into the capsule cavity and induces rotation of a capsule in the capsule cavity. The activated capsule then releases a dose of particles into the swirling inhalation airflow downstream through the mouthpiece to the consumer. Thus, the swirling inhalation airflow is created upstream from the inhaler article and swirling inhalation airflow enters the distal end or upstream-most end of the inhaler article.

An inhaler article comprises an elongated tubular body extending along an inhaler longitudinal axis from a mouthpiece end to a distal end. The mouthpiece end is the proximal end, or the downstream end. The distal end is the upstream end. A capsule cavity is defined within the body bounded downstream by a filter element and bounded upstream by an open tubular element defining a central passage. Prior to insertion into an inhaler article holder, the distal end of the inhaler article may be closed. After insertion into an inhaler article holder, the distal end of the inhaler article may be open. The distal end of the inhaler article may interact with complimentary structures in the inhaler article holder so that, upon introducing the inhaler article into the inhaler article holder, the distal end of the inhaler article may open. When introduced into the inhaler article holder, the distal end of the inhaler article has a central passage which forms an open air-inlet aperture extending from the distal end of the body to the capsule cavity. A capsule is disposed within the capsule cavity, the central passage may have a smaller diameter then the capsule. Thus, the capsule may not pass through the central passage and is retained within the capsule cavity.

The inhaler article holder includes a housing comprising a housing cavity for receiving an inhaler article and a sleeve configured to retain an inhaler article within the housing cavity. The housing cavity is defined by a single housing opening that extends into the housing to a closed end along a housing longitudinal axis. The single housing opening is configured to receive the inhaler article.

The sleeve is contained within the housing cavity and is movable along the housing longitudinal axis between a first position and a second position. The sleeve may be slidable along the housing longitudinal axis between a first position and a second position. In the first position the sleeve is located adjacent to the single housing opening. In the second position the sleeve is further away from the single housing opening a lateral distance along the longitudinal axis.

The sleeve extends from an open end to a closed end (or restricted end) and defines a cylindrical lumen along a longitudinal axis of the sleeve. The open end of the sleeve aligns with the single housing opening.

The sleeve closed end includes an airflow element and an aperture to allow the piercing element to pass through the closed end and extend into the sleeve lumen. The airflow element includes one or more inhalation air inlets that provide airflow communication from the annular space around the sleeve into the sleeve cylindrical lumen. This airflow element is configured to induce rotating or swirling inhalation airflow into the sleeve cylindrical lumen and directly into the inhaler article capsule cavity. This swirling or rotational inhalation airflow may be transmitted into an inhaler article to rotate a capsule and release dry powder contained within the capsule.

The airflow element of the sleeve includes a tubular element having a central passage in fluid communication with the sleeve cavity. The airflow element has at least one air inlet allowing inhalation air to enter into the central passage. The at least one air inlet extends in a direction that is tangential to the central passage to generate the swirling or rotational inhalation airflow.

The airflow element of the sleeve includes a tubular element having a central passage in fluid communication with the sleeve cavity. The airflow element has at least two air inlets allowing inhalation air to enter into the central passage. The at least two air inlets extend in a direction that is tangential to the central passage to generate the swirling or rotational inhalation airflow.

The airflow element of the sleeve includes a tubular element having a central passage in fluid communication with the sleeve cavity. The airflow element has at least three air inlets allowing inhalation air to enter into the central passage. The at least three air inlets extend in a direction that is tangential to the central passage to generate the swirling or rotational inhalation airflow.

The airflow element may include an aperture to receive and allow the piercing element to pass through the airflow element.

Inhalation air may enter the inhaler article holder through the open aperture receiving the inhaler article and travel into the housing cavity along the length of the inhaler article to the airflow element at the sleeve closed end. Alternatively, inhalation air may enter the inhaler article holder through air inlets through the housing surface.

The inhaler article holder may further include a piercing element fixed to and extending from a housing inner surface of the cavity. The piercing element includes a single solid shaft extending from a fixed end to a tip along the piercing element longitudinal axis. The piercing element is configured to extend through the closed end of the sleeve and into the sleeve cavity along a longitudinal axis of the housing. The piercing element contacts and pierces the capsule of a received inhaler article once the sleeve moves from the first position to the second position. Moving the sleeve from the second position to the first position removes the piercing element from the capsule and exposes an aperture in the capsule that allows dry particles contained within the capsule to be released from the capsule as inhalation air rotates the capsule.

The inhaler system or inhaler article holder piercing element described herein is a single piercing element that is offset from the longitudinal axis of the inhaler article holder. The piercing element is a single piercing element that is offset from the inhaler article holder movable sleeve receiving an inhaler article. The piercing element is a single piercing element that is offset from the capsule cavity containing a capsule. The piercing element is a single piercing element that is offset from the longitudinal axis of the capsule or axis of rotation of the capsule when the capsule spins during inhalation and consumption of the dry particles released from an activated capsule. The inhaler system has less than two piercing elements. The inhaler system forms less than two apertures in the capsule containing dry powder particles.

The inhaler system or inhaler article holder piercing element described herein is a single piercing element that strikes and pierces a hemispherical endcap of the capsule, contained within the capsule cavity of the inhaler device. The single piercing element strikes and pierces a hemispherical endcap of the capsule offset from the central longitudinal axis of the capsule and the central longitudinal axis of the sleeve and central longitudinal axis of the capsule cavity. The single piercing element strikes and pierces a hemispherical endcap of the capsule not at the central longitudinal axis of the capsule.

The piercing element shaft has a shaft diameter. The piercing element longitudinal axis is offset from the sleeve longitudinal axis or capsule cavity longitudinal axis by at least one piercing element diameter or at least one shaft diameter, or at least 1.5 piercing element diameters or at least 1.5 shaft diameters, or at least 2 piercing element diameters or at least 2 shaft diameters, or in a range from 1 to 2 piercing element diameters, or in a range from 1 to 2 shaft diameters.

The hemispherical endcap of the capsule has a radius of 0% at the central longitudinal axis of the capsule and a radius of 100% at the outer circumference of the hemispherical endcap of the capsule. The single offset piercing element pierces the capsule hemispherical endcap in a range from 25% to 90% of a capsule radius away from the capsule longitudinal axis, or from 33% to 80% of the capsule radius away from the capsule longitudinal axis, or 50% to 75% of the capsule radius away from the capsule longitudinal axis.

The hemispherical endcap of the capsule may have an outer radius in a range from 2.6 mm to 3.2 mm or about 3 mm. The piercing element pierces this capsule at the capsule curved end or hemispherical endcap at a radial distance of at least 1 mm from the capsule longitudinal axis, or in a range from about 1 mm to about 2.5 mm from the capsule longitudinal axis or in a range from about 1.5 mm to about 2.2 mm from the capsule longitudinal axis, or at about 2 mm from the capsule longitudinal axis.

The piercing element tip has only a single bevel or cutting plane. This single bevel or cutting plane is specifically oriented relative to the piercing element offset to achieve reliable and repeatable piercing without orientating or aligning the capsule relative to the piercing element.

The piercing element single bevel or cutting plane may define a planar surface opposing the sleeve longitudinal axis. The piercing element single bevel or cutting plane may define a planar surface opposing the capsule longitudinal axis. The piercing element single bevel or cutting plane defines a planar surface that may face a sleeve inner diameter surface closest to the planar surface. The piercing element single bevel may face toward the capsule. The piercing element single bevel may face away from the capsule.

The piercing element forms a single aperture in the capsule defining only a single hinge of capsule material extending into the capsule cavity. The single hinge of capsule material may be located at a point around the single aperture furthest from the capsule longitudinal axis.

The piercing element forms a single aperture in the capsule defining only a single hinge of capsule material extending into the capsule cavity. The hinge is formed when the beveled tip of the piercing element pierces the capsule. As the beveled tip of the piercing element enters the capsule, the beveled tip of the piercing element cuts the capsule to form an aperture. Then, as the beveled tip of the piercing element continues to enter the capsule, it continues to cut the capsule. The hinge is formed as the end of the bevel enters the capsule. When piercing element is then removed from the capsule, an aperture with a hinge is formed in the capsule. Thus, an aperture is formed in the capsule substantially related to the size of the piercing element, with the hinge formed in the aperture opposite the tip of the piercing element. If the piercing element single bevel faces toward the capsule, the hinge is formed at the inside edge of the aperture, where the inside edge is closer to the longitudinal axis of the capsule. If the piercing element single bevel faces away from the capsule, the hinge is formed at the outside edge of the aperture, where the outside edge is farther away from the longitudinal axis of the capsule. When the beveled tip of the piercing element faces away from the longitudinal axis of the capsule, a single hinge of capsule material is formed located at a point of the single aperture furthest from the capsule longitudinal axis.

The sleeve closed end may further include a sleeve bottom element substantially forming the closed end of the sleeve. The sleeve bottom element may be fixed and contact the airflow element. The sleeve bottom element may extend away from the airflow element a distance along the sleeve longitudinal axis and toward the closed end of the housing cavity. The sleeve bottom element may have an aperture that contains the piercing element and allows the piercing element to pass through the sleeve bottom element aperture.

The inhaler article holder may further include a spring element configured to bias the sleeve away from the piercing element. The spring element may bias the sleeve away from the second position to the first position. The spring element may be in a relaxed state in the sleeve first position. The spring element may be in a compressed state in the second position. Preferably the piercing element is disposed within the spring element.

The sleeve may include an elongated slot extending along a longitudinal length of the sleeve. The housing may further include a pin extending from an inner surface of the housing cavity. The pin may be configured to mate with the elongated slot to maintain alignment of the sleeve as it moved between the first and second positions.

An inner housing may be contained within the housing cavity. The inner housing may separate at least a portion of the sleeve from the inner surface of the housing cavity. The inner housing may separate a fixed end of the piercing element from the inner surface of the housing cavity. The inner housing may separate at the spring element from the inner surface of the housing cavity.

Inhalable powders may include various active agents. The active agent may comprise an alkaloid such as nicotine or anatabine or anabasine, for example. Preferably, the active agent comprises solid salt of an alkaloid, such as a nicotine salt.

The amount of active agent may be selected based on the desired or intended use of the inhalable dry powder. For example, the amount of active agent may be between 0.5 wt-% and 10 wt-% of the total weight of the dry powder particles. The dry powder particles may comprises 0.5 wt-% or more, 1 wt-% or more, 2 wt-% or more, or 3 wt-% or more of the active agent, and 12 wt-% or less, 10 wt-% or less, 9 wt-% or less, 8 wt-% or less, or 7 wt-% or less, of the active agent, or from 0.5 wt-% to 10 wt-%, from 1 wt-% to 8 wt-%, from 1.5 wt-% to 6 wt-%, or from 2 wt-% to 5 wt—of the active agent.

The dry powder particles may comprises 0.5 wt-% or more, 1 wt-% or more, 2 wt-% or more, or 3 wt-% or more of nicotine, and 12 wt-% or less, 10 wt-% or less, 9 wt-% or less, 8 wt-% or less, or 7 wt-% or less, of nicotine, or from 0.5 wt-% to 10 wt-%, from 1 wt-% to 8 wt-%, from 1.5 wt-% to 6 wt-%, or from 2 wt-% to 5 wt-% nicotine.

The amount of active agent may also be selected on a per-dose basis. The inhalable powder may be packaged in a single dose form or in a multiple dose form. For example, the inhalable powder may comprise 0.5 mg or more, 1 mg or more, 2 mg or more, or 5 mg or more of the active agent per dose. The inhalable powder may comprise 500 mg or less, 200 mg or less, 100 mg or less, 50 mg or less, 20 mg or less, or 10 mg or less of the active agent per dose. In some embodiments, the inhalable powder comprises from 0.01 to 10 mg of anatabine or nicotine or anabasine per dose, 0.05 to 5 mg anatabine or nicotine or anabasine per dose, or 0.1 to 1 mg of anatabine or nicotine or anabasine per dose.

In embodiments, the capsule contains from 1 to 20 doses. In embodiments, the capsule contains from 1 to 10 doses. In embodiments the capsule contains from 10 to 20 doses. In embodiments, the capsule contains 1 dose. In embodiments, the capsule contains 2 doses. In embodiments, the capsule contains 3 doses. In embodiments, the capsule contains 4 doses. In embodiments, the capsule contains 5 doses. In embodiments, the capsule contains 6 doses. In embodiments, the capsule contains 7 doses. In embodiments, the capsule contains 8 doses. In embodiments, the capsule contains 9 doses. In embodiments, the capsule contains 10 doses. In embodiments, the capsule contains 11 doses. In embodiments, the capsule contains 12 doses. In embodiments, the capsule contains 13 doses. In embodiments, the capsule contains 14 doses. In embodiments, the capsule contains 15 doses. In embodiments, the capsule contains 16 doses. In embodiments, the capsule contains 17 doses. In embodiments, the capsule contains 18 doses. In embodiments, the capsule contains 19 doses. In embodiments, the capsule contains 20 doses.

The dry powder particles may have a particle size of 20 µm or less, 10 µm or less, or 5 µm or less, or 0.1 µm or greater, 0.2 µm or greater, or 0.5 µm or greater, or ranging from 0.5 µm to 10 µm, or from 0.75 µm to 5 µm, or from 1 µm to 5 µm, or from 1 µm to 3 µm, or from 1.5 µm to 2.5 µm. The desired particle size range may be achieved by spray drying, milling, sieving, or a combination thereof.

The dry powder particles may be further mixed with a second population of particles to form a powder system. Preferably, the second population of particles have a different particle size or larger particle size than the dry powder particles. For example, the second population of particles may have a particle size of about 20 µm or greater, or about 50 µm or greater, 200 µm or smaller, 150 µm or smaller, or in a range from 50 µm to 200 µm, or from 50 µm to 150 µm.

The second population of particles may have any useful size distribution for inhalation delivery selectively into the mouth or buccal cavity of a user. The larger second population of flavourant particles may assist in delivery of the dry powder particles to the inhalation airflow to the user.

The dry powder particles and second population of particles may be combined in any useful relative amount so that the second population of particles are detected by the user when consumed with the dry powder particles. Preferably, the dry powder particles and second population of particles form at least about 90 wt-% or at least about 95 wt-% or at least about 99 wt-% or 100 wt-% of the total weight of the powder system.

The dry powder particles may be mixed with a second population of flavourant particles to form a powder system. Preferably, the second population of flavourant particles have a different particle size or larger particle size than the dry powder particles. For example, the flavor particles may have a particle size of about 20 µm or greater, or about 50 µm or greater, 200 µm or smaller, 150 µm or smaller, or in a range from 50 µm to 200 µm, or from 50 µm to 150 µm. The second population of flavourant particles may have any useful size distribution for inhalation delivery selectively into the mouth or buccal cavity of a user. The larger second population of flavourant particles may assist in delivery of the dry powder particles to the inhalation airflow to the user.

The dry powder particles and second population of flavourant particles may be combined in any useful relative amount so that the second population of flavourant particles are detected by the user when consumed with the dry powder particles. Preferably, the dry powder particles and second population of flavourant particles form at least about 90 wt-% or at least about 95 wt-% or at least about 99 wt-% or 100 wt-% of the total weight of the powder system.

The dry powder particles or powder system may be provided in a suitable dosage form. For example, the dry powder particles or powder system may be provided in a capsule. The dosage form (for example, capsule) may be configured for use in a suitable inhaler. For example, the capsule may be utilized in an inhaler device having a capsule cavity. Air flow management through a capsule cavity of the inhaler device may cause a capsule contained therein to rotate during inhalation and consumption. The capsule may contain dry powder particles or powder system.

The term "particle size" is used here to refer to the mass median aerodynamic diameter (MMAD) of the particle or set of particles, unless otherwise stated. Such values are based on the distribution of the aerodynamic particle diameters defined as the diameter of a sphere with a density of 1 $gm/cm^3$ that has the same aerodynamic behavior as the particle which is being characterized.

In particular, for a powder system reference is commonly made to the mass median aerodynamic diameter (MMAD), one of the metrics most widely adopted as a single number descriptor of aerodynamic particle-size distribution. The MMAD is a statistically derived figure for a particle sample: by way of example, an MMAD of 5 micrometres means that 50 percent of the total sample mass will be present in particles having aerodynamic diameters of less than 5 micrometres, and that the remaining 50 percent of the total sample mass will be present in particles having an aerodynamic diameter greater than 5 micrometres. In the context of the present invention, when describing a powder system, the term "particle size" preferably refers to the MMAD of the powder system.

The MMAD of a powder system is preferably measured with a cascade impactor. Cascade impactors are instruments which have been extensively used for sampling and separating airborne particles for determining the aerodynamic size classification of aerosol particles. In practice, cascade impactors separate an incoming sample into discrete fractions on the basis of particle inertia, which is a function of particle size, density and velocity. A cascade impactor typically comprises a series of stages, each of which comprises a plate with a specific nozzle arrangement and a collection surface. As nozzle size and total nozzle area both decrease with increasing stage number, the velocity of the sample-laden air increases as it proceeds through the instrument. At each stage, particles with sufficient inertia break free from the prevailing air stream to impact on the collection surface. Therefore, at any given flow rate, each stage is associated with a cut-off diameter, a figure that defines the size of particles collected. With increasing stage number, velocity increases and so stage cut-off diameter decreases. Thus, the cut-off diameter associated with a given stage is a function of the air-flow rate used for testing. To reflect in-use performance, nebulisers are routinely tested at 15 L/min and dry powder inhalers may be tested at flow rates up to 100 L/min.

Preferably, in the context of the present invention, the MMAD of a powder system is measured with a Next Generation Impactor (NGI) 170 (available from Copley Scientific AG). The NGI is a high performance, precision, particle classifying cascade impactor having seven stages plus a Micro-Orifice Collector (MOC). Characteristics and operation principle of a NGI are described, for example, in Marple et al., Journal of Aerosol Medicine—Volume 16, Number 3 (2003). More preferably, measurements are carried out at 20±3 degrees Celsius and relative humidity of 35±5 percent.

A dry powder formulation typically contains less than or equal to about 15 percent by weight moisture, preferably less than or equal to about 10 percent moisture, even more preferably less than or equal to about 6 percent by weight moisture. Most preferably a dry powder formulation contains less than or equal to about 5 percent by weight moisture or even less than or equal to about 3 percent by weight moisture or even less than or equal to about 1 percent by weight moisture.

According to an aspect of the present invention, there is provided a method of assembling an inhaler article holder having an oriented piercing element, comprising, inserting an inner housing into a jig. The inner housing extends along a longitudinal axis from a proximal end to a distal end an inner housing length. The distal end comprising a piercing element aperture. The inner housing length mates with a jig opening. The jig comprising a jig angled planar surface coaxial with the piercing element aperture. The method includes mating a piercing element cutting plane with the jig angled planar surface. The piercing element extending from a proximal cutting end along a piercing element longitudinal axis to the piercing element distal end. The piercing element cutting plane defines the piercing element proximal cutting end. The piercing element distal end is received in the inner housing piercing element aperture, and then fixing the piercing element distal end to the inner housing. Wherein the piercing element cutting plane is orientated relative to the inner housing longitudinal axis.

The fixing step may include fixing the piercing element distal end to the inner housing with an adhesive. The adhesive may be a curable adhesive. The adhesive may be a radiation curable adhesive. The adhesive may be a light curable adhesive. The adhesive may be a heat curable adhesive. The fixing step locks the orientation of the piercing element cutting plane relative to the offset of the longitudinal axis of the piercing device from the central longitudinal axis of the sleeve member.

The mating step may include sliding the piercing element into the jig until the piercing element cutting plane contacts the jig angled planar surface and rotating the piercing element until the piercing element cutting plane mates with the jig angled planar surface. The piercing element may rotate to mate with the jig angled planar surface as a function of the interaction between the jig and the piercing element without a separate rotating step. The piercing element may be placed into the jig and mated with the jig angled planar surface before the inner housing is placed into the jig.

Alternatively, the piercing element may be placed into the jig and mated with the jig angled planar surface after the inner housing is placed into the jig. Here the inner housing may be inserted into the jig and the piercing element distal end slides into the inner housing piercing element aperture after the piercing element cutting plane is mated with the with the jig angled planar surface.

The jig includes a piercing element aperture that is coaxial with the jig angled planar surface and the inner housing piercing element aperture. The jig is configured to mate with and secure the piercing element and mate with and secure the inner housing.

The method may further include fixing a spring element distal end to the inner housing distal end and fixing a sleeve member distal end to a spring element proximal end and forming an inner housing assembly. The sleeve member distal end comprising a sleeve closed distal end having a piercing element aperture. The piercing element may extend within the spring element and through the sleeve piercing element aperture. The sleeve member slides along the inner housing between a first compressed position and a second relaxed position.

When the piercing element cutting plane is mated with the jig angled planar surface after the inner housing is inserted into the jig, the inner housing may be inserted into the jig and the piercing element slides into the inner housing piercing element aperture before the piercing element cutting plane is mated with the with the jig angled planar surface. In this embodiment, the inserting step may include inserting an inner housing having a spring element distal end fixed to the inner housing distal end and a sleeve member distal end fixed to a spring element proximal end to from the inner housing assembly. The sleeve member distal end may include a closed sleeve distal end having a piercing element aperture. The piercing element may extend within the spring element and through the sleeve piercing element aperture. The sleeve member may slide along the inner housing between a first compressed position and a second relaxed position.

The sleeve member extends along a sleeve longitudinal axis from the sleeve member closed distal end to the sleeve member open proximal end. The piercing element longitudinal axis is parallel with but offset from the sleeve longitudinal axis, as described above. The piercing element cutting plane is orientated facing 180 degrees from the sleeve longitudinal axis utilizing the jig described herein.

Once the inner housing assembly is formed, the inner housing assembly can be placed into an outer housing, forming a holder for an inhaler device.

All values reported as a percentage are presumed to be weight percent based on the total weight.

All scientific and technical terms used herein have meanings commonly used in the art unless otherwise specified.

The definitions provided herein are to facilitate understanding of certain terms used frequently herein.

As used herein, the singular forms "a", "an", and "the" encompass embodiments having plural referents, unless the content clearly dictates otherwise.

As used herein, "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open-ended sense, and generally mean "including, but not limited to". It will be understood that "consisting essentially of", "consisting of", and the like are subsumed in "comprising," and the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure, including the claims.

The term "substantially" as used here has the same meaning as "significantly," and can be understood to modify the relevant term by at least about 90%, at least about 95%, or at least about 98%. The term "not substantially" as used here has the same meaning as "not significantly," and can be understood to have the inverse meaning of "substantially," i.e., modifying the relevant term by not more than 10%, not more than 5%, or not more than 2%.

The invention is defined in the claims. However, below there is provided a non-exhaustive listing of non-limiting examples. Any one or more of the features of these examples may be combined with any one or more features of another example, embodiment, or aspect described herein.

Example Ex1. A method of assembling an inhaler article holder having an oriented piercing element, comprising, inserting an inner housing into a jig. The inner housing extends along a longitudinal axis from a proximal end to a distal end an inner housing length. The distal end comprising a piercing element aperture. The inner housing length mates with a jig opening. The jig comprising a jig angled planar surface coaxial with the piercing element aperture. The method includes mating a piercing element cutting plane with the jig angled planar surface. The piercing element extending from a proximal cutting end along a piercing element longitudinal axis to the piercing element distal end. The piercing element cutting plane defines the piercing element proximal cutting end. The piercing element distal end is received in the inner housing piercing element aperture, and then fixing the piercing element distal end to the inner housing. Wherein the piercing element cutting plane is orientated relative to the inner housing longitudinal axis.

Example Ex2. The method of Ex1, wherein the piercing element is parallel with but offset from the longitudinal axis of the inhaler device or capsule cavity Example Ex3. The method of any preceding Example, wherein the fixing step comprises fixing the piercing element distal end to inner housing with an adhesive.

Example Ex4. The method of any preceding Example, wherein the mating step comprises sliding the piercing element into the jig until the piercing element cutting plane contacts the jig angled planar surface and rotating the piercing element until the piercing element cutting plane mates with the jig angled planar surface.

Example Ex5. The method of any preceding Example, wherein the jig comprises a piercing element aperture that is coaxial with jig angled planar surface and the inner housing piercing element aperture.

Example Ex6. The method of any preceding Example, wherein the piercing element cutting plane is mated with the with the jig angled planar surface before the inner housing is inserted into the jig.

Example Ex7. The method of Ex6, wherein the inner housing is inserted the jig and the piercing element distal end slides into the inner housing piercing element aperture after the piercing element cutting plane is mated with the with the jig angled planar surface.

Example Ex8. The method of any preceding Example, further comprising fixing a spring element distal end to the inner housing distal end and fixing a sleeve member distal end to a spring element proximal end and forming an inner housing assembly, the sleeve member distal end comprising a sleeve closed distal end having a piercing element aperture, the piercing element extending within the spring element and through the sleeve piercing element aperture, the sleeve member slides along the inner housing between a first compressed position and a second relaxed position.

Example Ex9. The method of any of Ex1 to Ex5, wherein the piercing element cutting plane is mated with the with the jig angled planar surface after the inner housing is inserted into the jig.

Example Ex10. The method of Ex9, wherein the inner housing is inserted into the jig and the piercing element slides into the inner housing piercing element aperture before the piercing element cutting plane is mated with the with the jig angled planar surface.

Example Ex11. The method of any of Ex9 or Ex10, wherein the inserting step comprises inserting an inner housing comprising a spring element distal end fixed to the inner housing distal end and a sleeve member distal end fixed to a spring element proximal end and forming an inner housing assembly, the sleeve member distal end comprising a closed sleeve distal end having a piercing element aperture, the piercing element extending within the spring element and through the sleeve piercing element aperture, the sleeve member slides along the inner housing between a first compressed position and a second relaxed position.

Example Ex12. The method of any of Ex8 or Ex11, wherein the sleeve member extends along a sleeve longitudinal axis from the sleeve member closed distal end to the sleeve member open proximal end, the piercing element longitudinal axis is parallel with but offset from the sleeve longitudinal axis.

Example Ex13. The method of Ex12, wherein the piercing element cutting plane is orientated facing 180 degrees from the sleeve longitudinal axis.

Example Ex14. The method of any of Ex8 or Ex11, wherein further comprising fixing the inner housing assembly to an outer housing, forming a holder for an inhaler device.

Example Ex15. The method of Ex11, wherein the outer housing contains the assembled inner housing and defines an inhaler article opening to receive an inhaler article.

Example Ex16. The method of any preceding Example, wherein the proximal cutting end of the piercing element has only a single cutting plane.

Example Ex17. The method of any of Ex12 or Ex13, wherein the piercing element cutting plane is orientated to oppose the sleeve longitudinal axis.

Example Ex18. The method of any of Ex12 or Ex13, wherein the piercing element cutting plane defines a planar surface facing a sleeve inner diameter surface closest to the planar surface.

The Examples will now be further described with reference to the figures in which.

Figure 5:
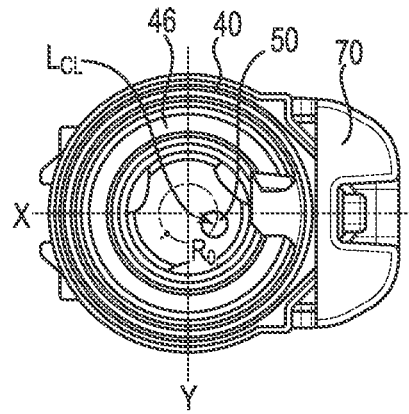
Figure 6A:
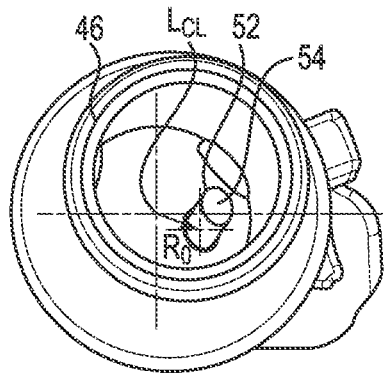
Figure 7:
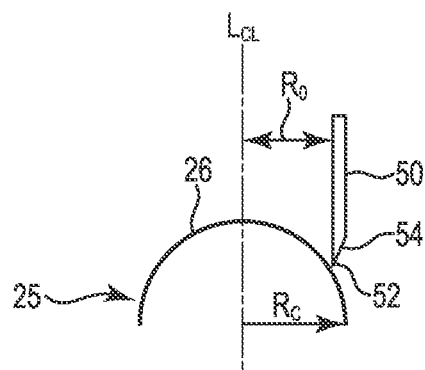
Figure 6B:
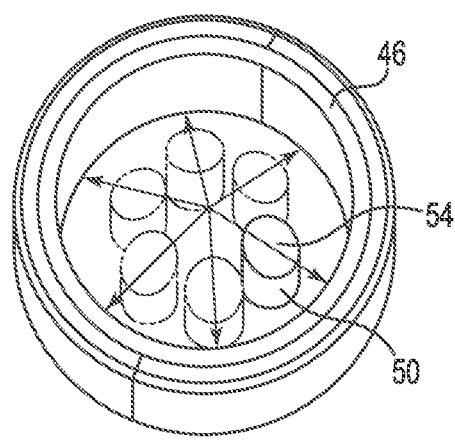
Figure 10:
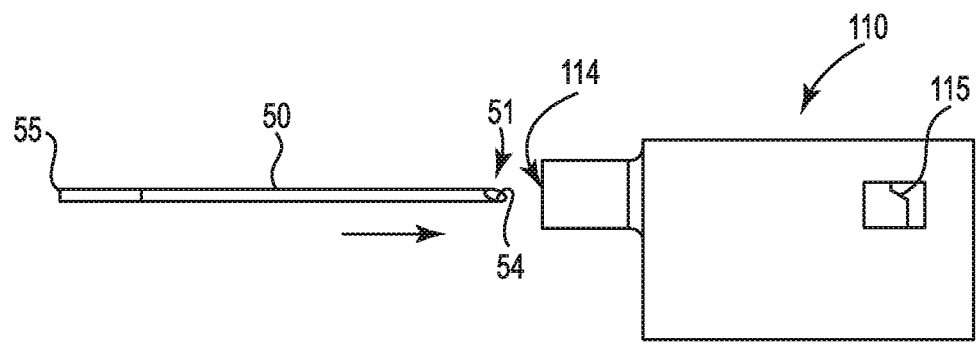
Figure 11:
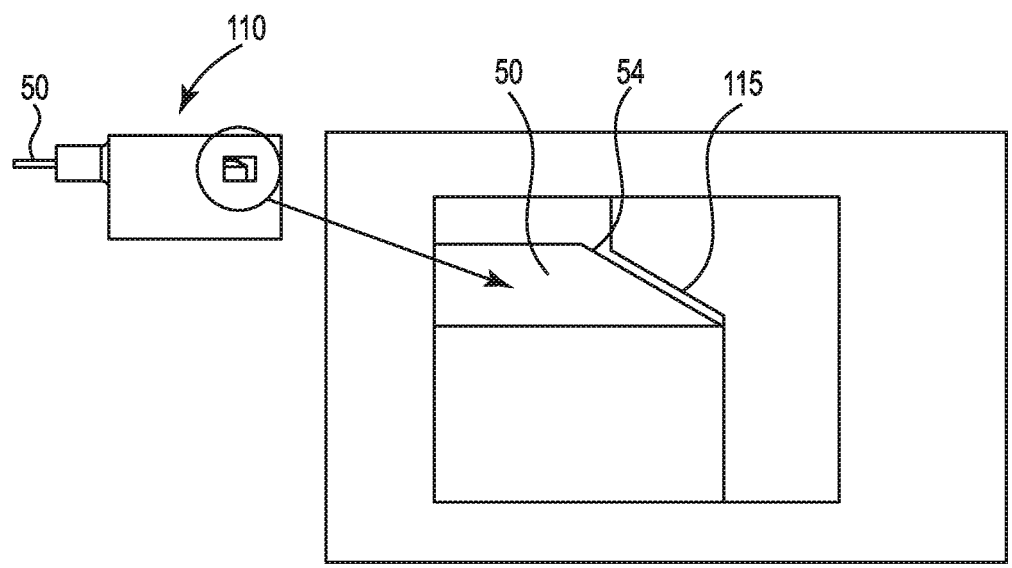
Figure 12:
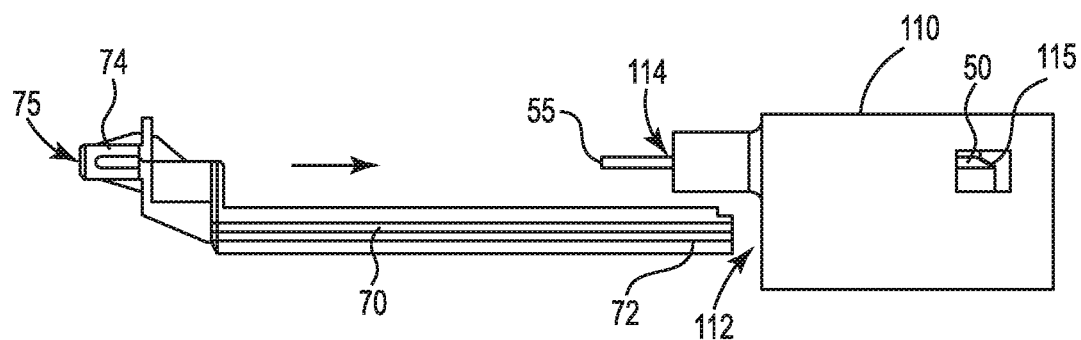
Figure 13:
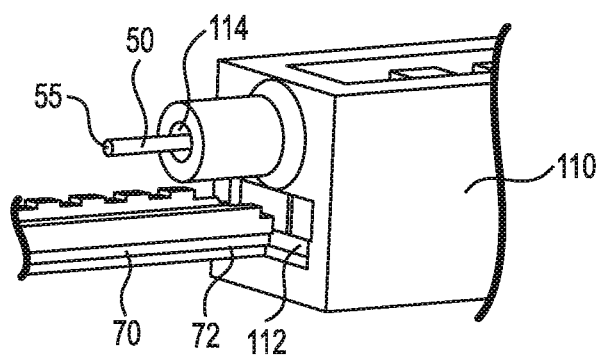
Figure 14:
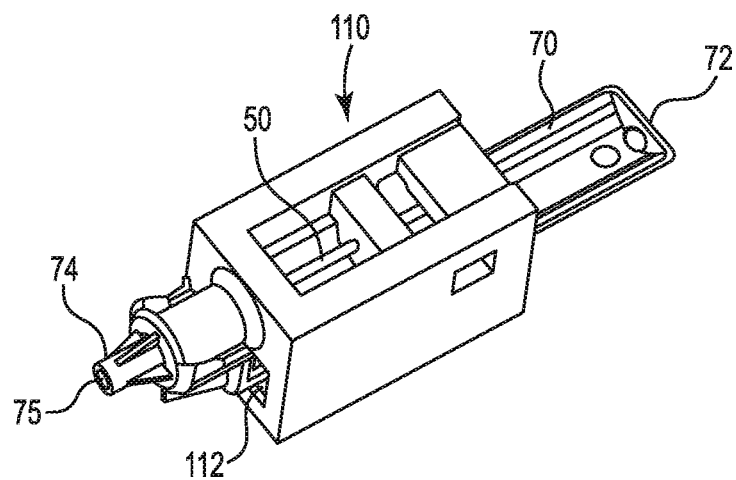
Figure 15:
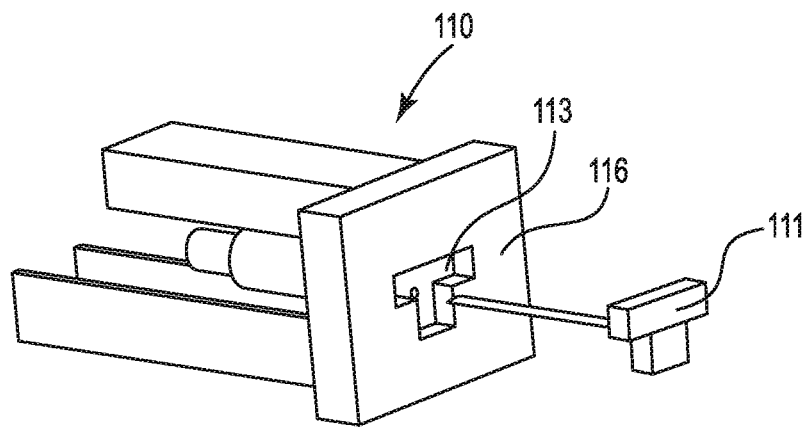
Figure 16:
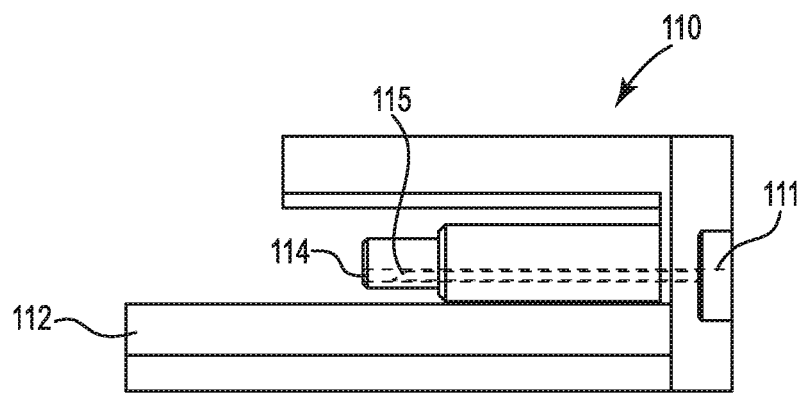
Figure 17:
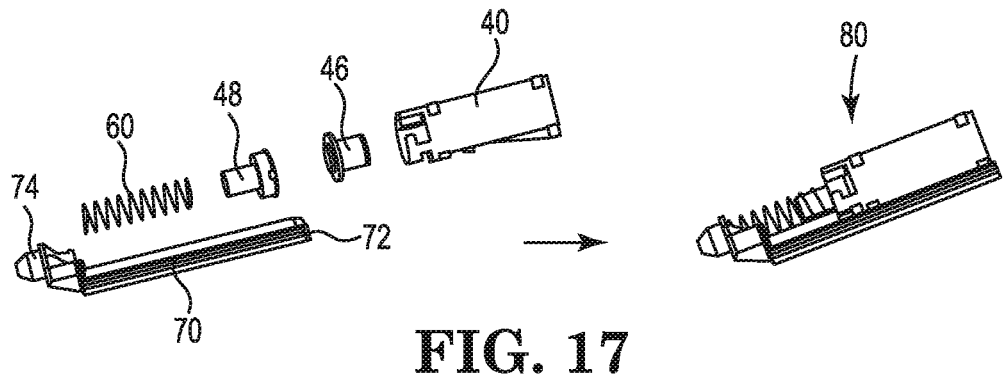
Figure 18:
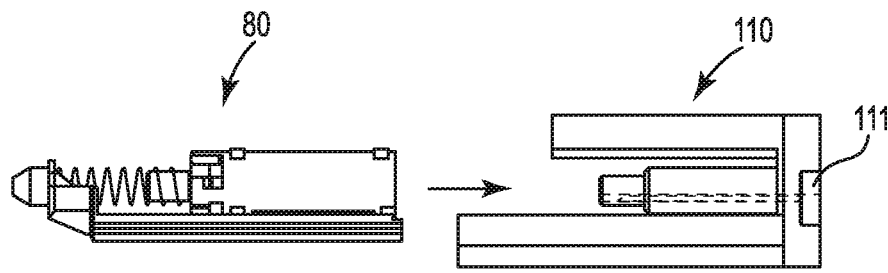
Figure 19:
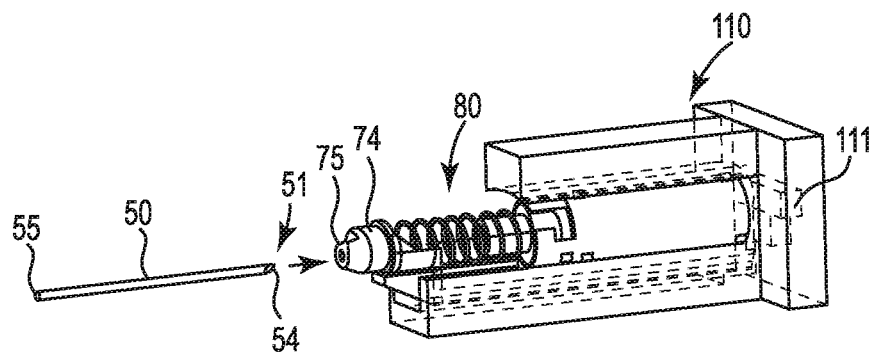

FIG. 5 a front elevation into the sleeve of an illustrative inhaler article holder;

FIG. 6A is a perspective view of an illustrative airflow element with piercing element;

FIG. 6B is a perspective view of an airflow element illustrating six alternative piercing element offset locations about the centerline of the airflow element;

FIG. 7 is a schematic cross-sectional diagram of an illustrative piercing element contacting a capsule endcap;

FIG. 8 is a schematic cross-sectional diagram of an illustrative capsule cavity with a capsule and piercing element;

FIG. 9A is a front elevation view of an illustrative capsule endcap after being pierced by the piercing element described herein;

FIG. 9B is a front elevation view of another illustrative capsule endcap after being pierced by the piercing element described herein;

FIG. 10 to FIG. 12 are side elevation schematic diagrams of a first assembly method;

FIG. 13 is a front perspective schematic diagram view of the first assembly method;

FIG. 14 is a top perspective schematic diagram view of the first assembly method;

FIG. 15 is a rear perspective schematic diagram view of a second assembly method;

FIG. 16 is a side elevation transparent schematic diagram view of the second assembly method;

FIG. 17 is a perspective view of an exploded to assembled inner housing assembly;

FIG. 18 is a side elevation schematic diagrams of the second assembly method;

FIG. 19 is a perspective view of the second assembly method; and

Figure 20:
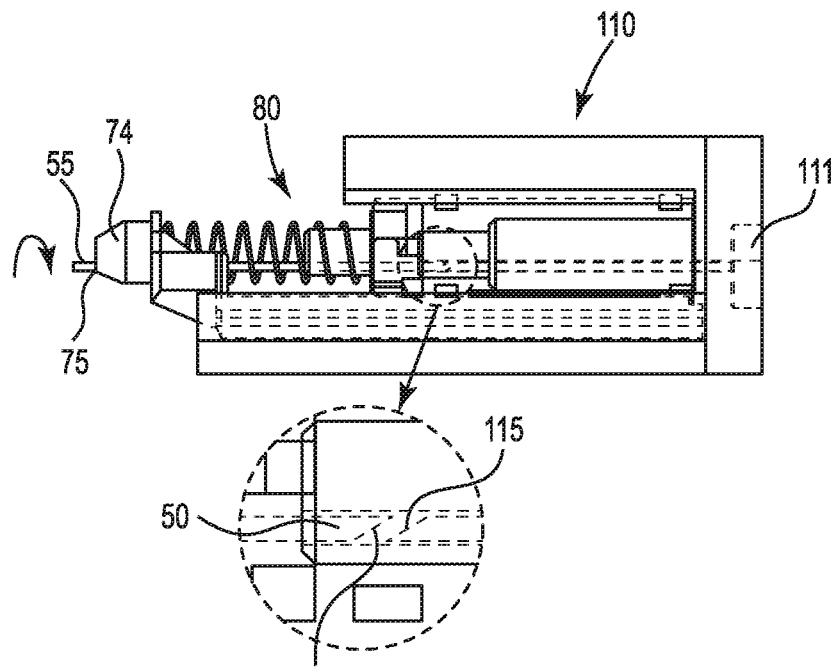
Figure 21:
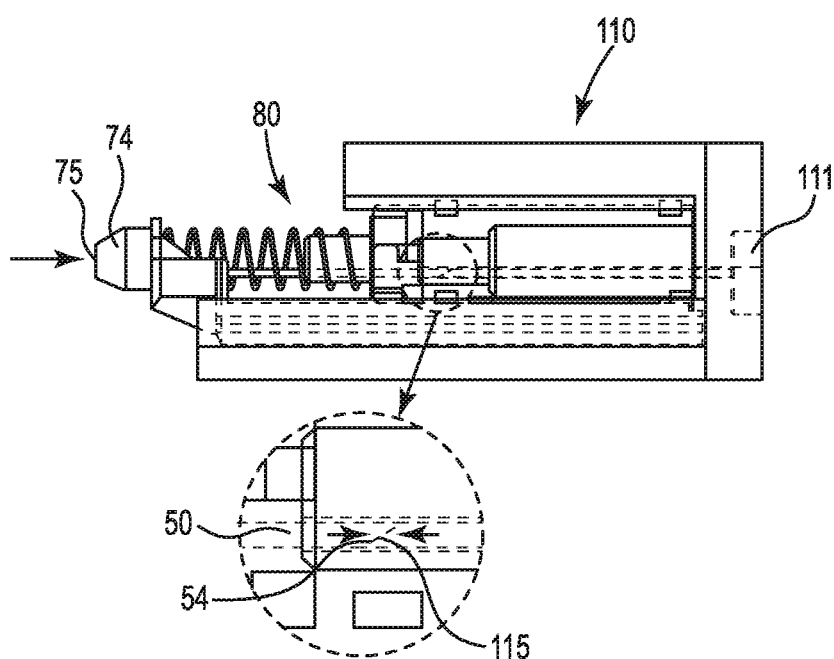

FIG. 20 and FIG. 21 are side elevation schematic diagrams of the second assembly method.

The schematic drawings are not necessarily to scale and are presented for purposes of illustration and not limitation. The drawings depict one or more aspects described in this disclosure. However, it will be understood that other aspects not depicted in the drawing fall within the scope and spirit of this disclosure.

Figure 1:
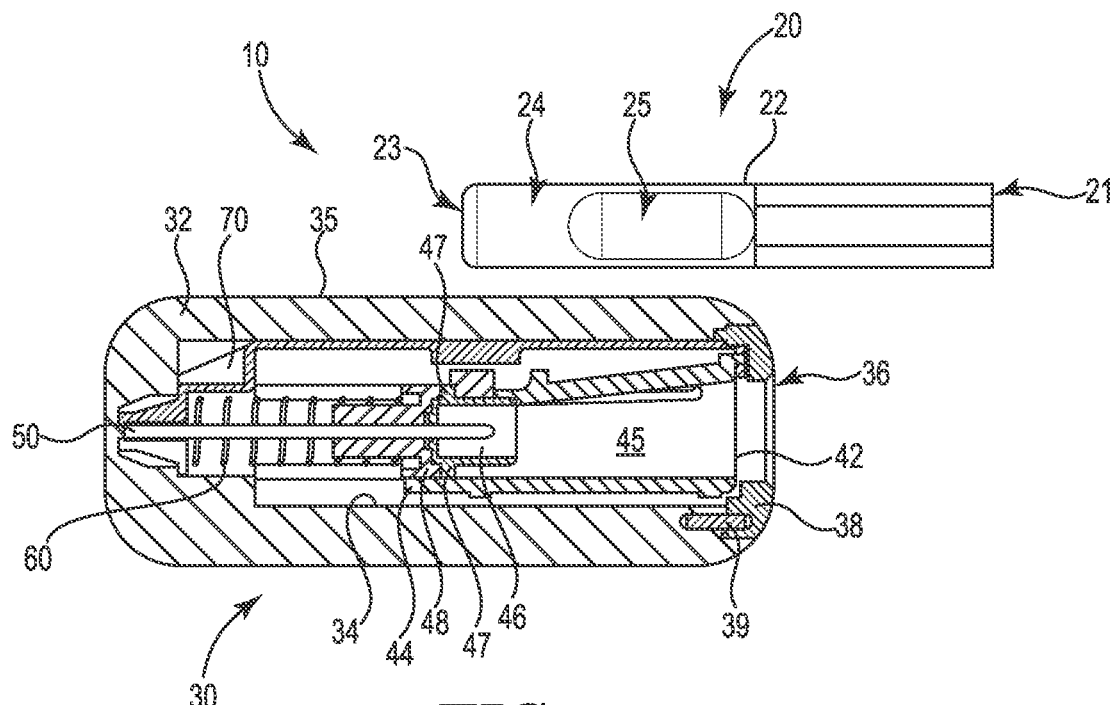
FIG. 1 is a schematic cross-sectional diagram of an illustrative inhaler system.
Figure 2:
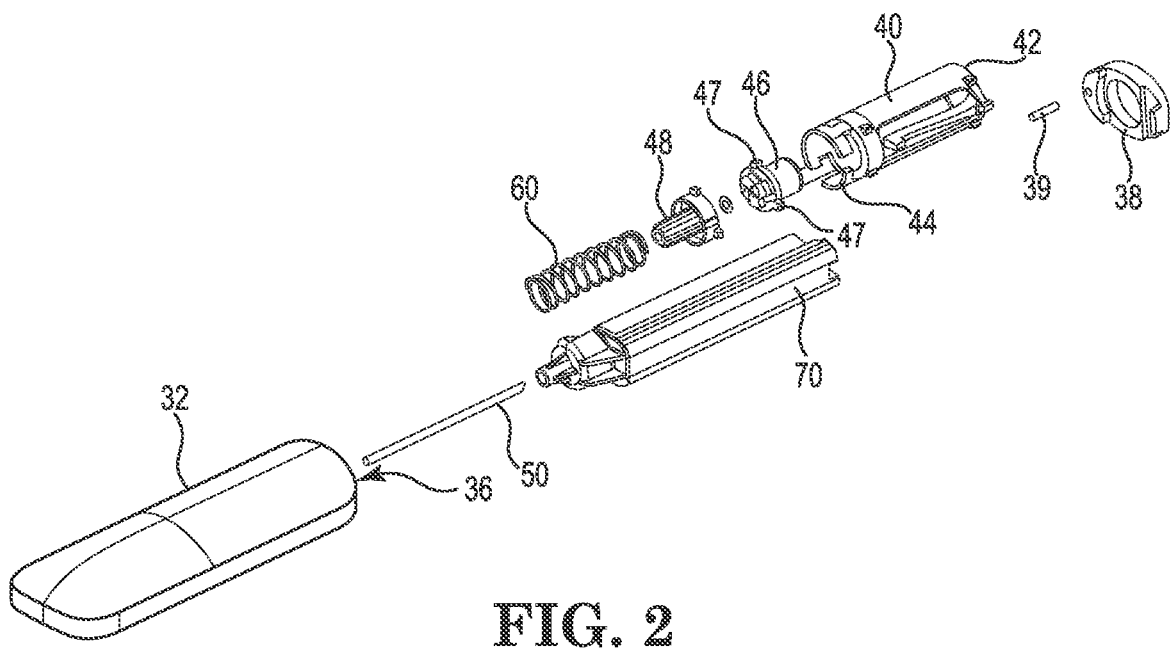
FIG. 2 is perspective exploded view of an illustrative inhaler article holder.
Figure 3A:
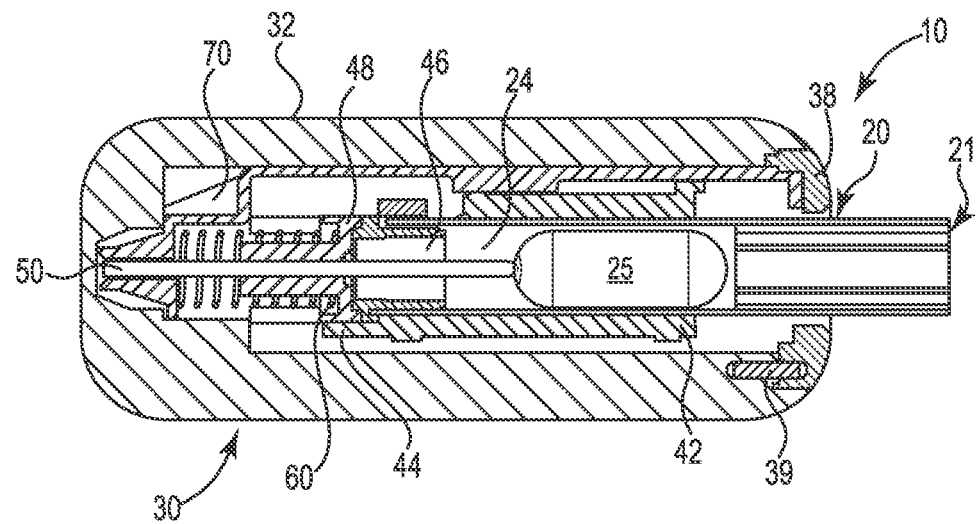
FIG. 3A is a schematic cross-sectional diagram of an illustrative inhaler system where the inhaler article is received in the inhaler article holder and piercing the capsule in a second position.
Figure 3B:
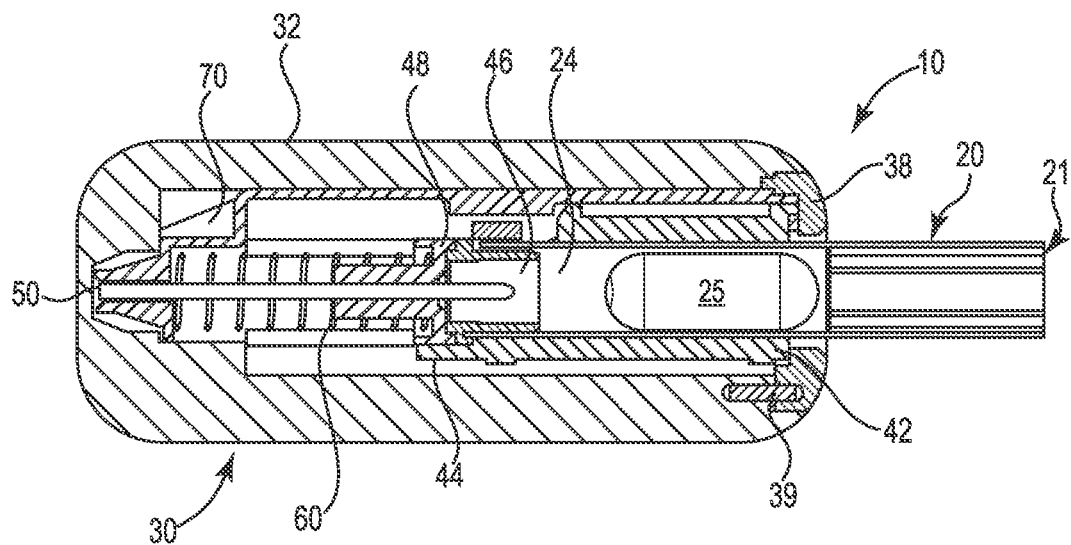
FIG. 3B is a schematic cross-sectional diagram of the illustrative inhaler system of FIG. 3A where the piercing element is retracted from the capsule in a first position.
Figure 4:
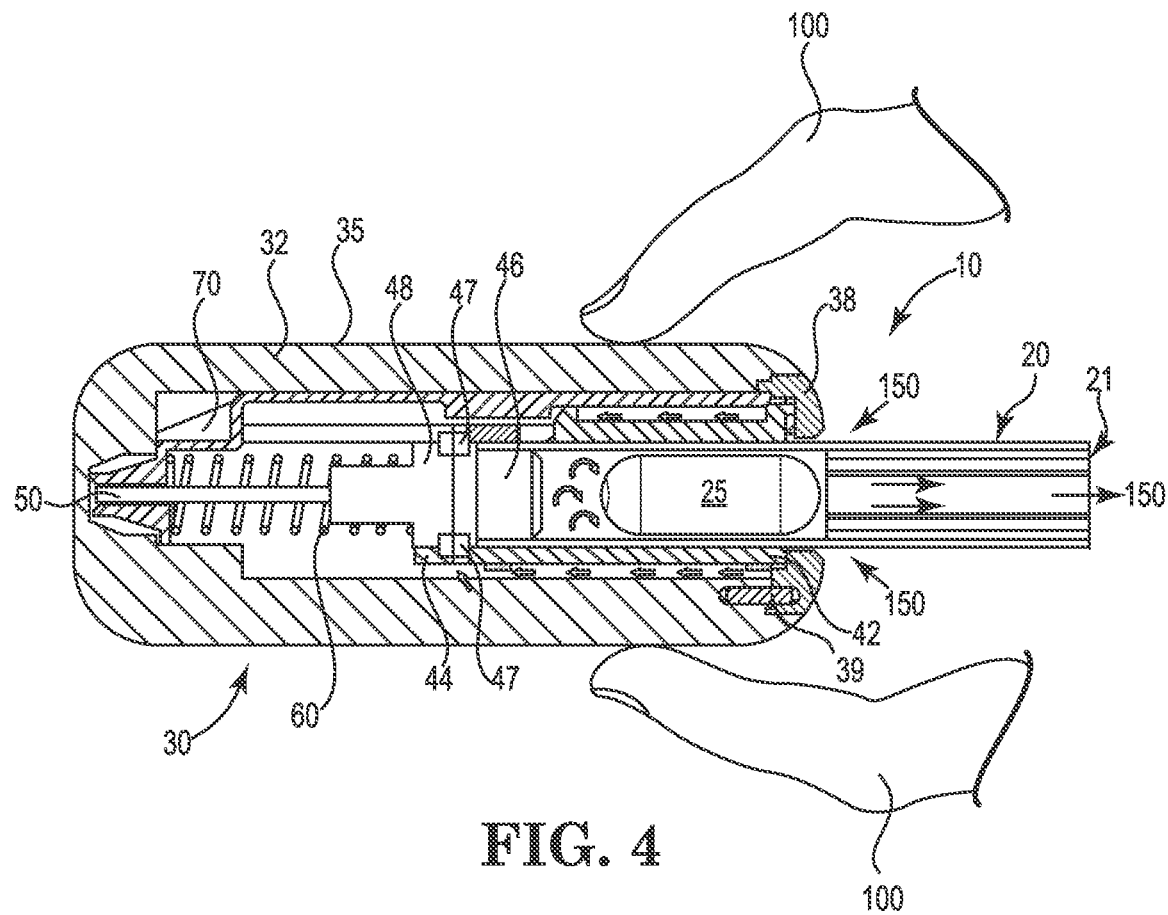
FIG. 4 is another schematic cross-sectional diagram of FIG. 3B illustrating the inhalation airflow path through the inhaler system.

FIG. 1 is a schematic cross-sectional diagram of an illustrative inhaler system 10. FIG. 2 is perspective exploded view of an illustrative inhaler article holder 30. FIG. 3A is a schematic cross-sectional diagram of an illustrative inhaler system 10 where the inhaler article 20 is received in the inhaler article holder 30 and piercing the capsule 25 in a second or compressed position. FIG. 3B is a schematic cross-sectional diagram of the illustrative inhaler system 10 of FIG. 3A where the piercing element 50 is retracted from the capsule 25 in a first or relaxed position. FIG. 4 is another schematic cross-sectional diagram of FIG. 3B illustrating the inhalation airflow 150 path (arrows) through the inhaler system 10.

The inhaler article holder 30 is configured to receive a separate consumable inhaler article 20 and induce swirling inhalation airflow into and through an inhaler article 20 during consumption. The inhaler article holder 30 and an inhaler article 20 form an inhaler system 10. The inhaler article 20 remains in the inhaler article holder 30 during use by the consumer. The inhaler article holder 30 is configured to induce swirling inhalation airflow entering the received inhaler article 20.

The illustrative inhaler article 20 includes a body 22 extending from a mouthpiece end 21 to a distal end 23. A capsule cavity 24 is defined within the body 22. A capsule 25 is contained within the capsule cavity 24. Dry powder particles described above may be contained within the capsule 25. The capsule 25 may be pierced to form an aperture through the body of the capsule and inhalation air may flow through the inhaler article 20 to release dry powder particles from the pierced capsule 25 and into the inhalation airflow and out of the mouthpiece end 21.

The inhaler article holder 30 includes a housing 32 defining a housing cavity defined by a housing inner surface 34, and an outer surface 35. A sleeve 40 is positioned within the housing cavity. The sleeve 40 is arranged to receive an inhaler article 20 and the sleeve 40 is movable within the housing cavity between a first position and a second position, along a longitudinal axis of the housing cavity.

A piercing element 50 is arranged to pierce the capsule 25 within the inhaler article 20 received within the sleeve 40 when the sleeve 40 is in the second position as illustrated in FIG. 3A.

The piercing element 50 may be configured to extend into the sleeve 40 along a longitudinal axis of the housing 32. The inhaler article holder 30 may include a spring element 60 configured to bias the sleeve 40 and any received inhaler article 20 away from the piercing element 50.

The sleeve 40 extends from an open end 42 to a closed end 44 (or restricted end) and defines a sleeve cavity 45 or cylindrical lumen 45 along a longitudinal axis of the sleeve 40. The open end 42 of the sleeve aligns with the single housing opening 36.

The sleeve closed end 44 includes an airflow element 46 and an aperture to allow the piercing element to pass through the closed end 44 and extend into the sleeve lumen 45. The airflow element 46 includes one or more inhalation air inlets 47 that provide airflow communication from the annular space around the sleeve 40 into the sleeve cylindrical lumen 45. This airflow element 46 is configured to induce rotating or swirling inhalation airflow into the sleeve cylindrical lumen 45 and directly into the inhaler article capsule cavity 24. This swirling or rotational inhalation airflow may be transmitted into an inhaler article 20 to rotate a capsule 25 and release dry powder contained within the capsule 25.

The airflow element 46 of the sleeve 40 includes a tubular element having a central passage in fluid communication with the sleeve cavity 45. The airflow element 46 has at least one air inlet 47 allowing inhalation air 150 to enter into the central passage. The at least one air inlet 47 extends in a direction that is tangential to the central passage to generate the swirling or rotational inhalation airflow.

The sleeve 40 includes a tubular element that may extend into the sleeve cavity 45 about 5 mm and have an outer diameter of about 5.5 mm and an inner diameter of about 4 mm. The received inhaler article 20 open distal end 23 may have an inner diameter of about 5.5 mm to provide an interference fit with the airflow element 46 tubular element.

The sleeve closed end 44 may further include a sleeve bottom element 48 substantially forming the closed end of the sleeve 40. The sleeve bottom element 48 may be fixed and contact the airflow element 46. The sleeve bottom element 48 may extend away from the airflow element 46 a distance along the sleeve longitudinal axis and toward the closed end of the housing cavity. The sleeve bottom element 48 may have an aperture that contains the piercing element 50 and allows the piercing element 50 to pass through the sleeve bottom element 48 aperture.

An inner housing 70 may be contained within the housing cavity. The inner housing 70 may separate at least a portion of the sleeve 40 from the inner surface of the housing cavity. The inner housing 70 may separate a fixed end of the piercing element 50 from the inner surface of the housing cavity. The inner housing 70 may separate the spring element 60 from the inner surface of the housing cavity.

An annular cover 38 may secure the inner housing 70 and sleeve 40 into the housing cavity. The annular cover 38 defines the single housing opening 36 for receiving the inhaler article 20. The annular cover 38 may be fixed to the housing 32 with a pin element 39.

FIG. 4 illustrates the inhalation airflow 150 path through the inhaler system 10. Inhalation airflow 150 enters the inhaler article holder 30 along the outer surface of the received inhaler article 20 and the annular cover 38. Once inside the housing cavity, the inhalation air 150 travels along the sleeve 40 length to the closed end 44 of the sleeve 40. The inhalation air 150 then enters the air inlet 47 of the airflow element 46 and forms swirling or rotating inhalation air 150 within the sleeve lumen 45. This swirling or rotating inhalation air is then directly transmitted into the distal end 23 of the inhaler article 20 and into the capsule cavity 24. The swirling inhalation airflow rotates or agitates the capsule 25 and dry powder particles are entrained in the inhalation airflow. The entrained inhalation airflow then flows out of the inhaler article via the mouthpiece end 21 and to the user 100. The inhalation airflow 150 path is illustrated in FIG. 4 with arrows.

FIG. 5 a front elevation into the sleeve 40 of an illustrative inhaler article holder. FIG. 6A is a perspective view of an illustrative airflow element 46 with piercing element 50. FIG. 6B is a perspective view of an airflow element 46 illustrating six alternative piercing element 50 offset locations about the centerline of the airflow element 46.

The single cutting plane or bevel 54 is offset from or spaced away from and opposes or faces away from the centerline of the airflow element 46. FIG. 6B illustrates solid line embodiment and five phantom line alternative piercing element 50 offset locations about the centerline of the airflow element 46. Each alternative location illustrates that the single cutting plane or bevel 54 is offset from or spaced away from and opposes or faces away from the centerline of the airflow element 46.

The central longitudinal axis $L_{CL}$ of the sleeve 40 is located at the intersection of the X and Y axis. The airflow element 46 defines the closed end of the sleeve 40. An inner housing 70 is fixed to the sleeve 40. The piercing element 50 extends through the airflow element 46 and is offset from the central longitudinal axis $L_{CL}$ a distance $R_O$. The central longitudinal axis $L_{CL}$ of the airflow element 46 is aligned with and co-incident with the central longitudinal axis $L_{CL}$ of the sleeve 40. The cutting end of the piercing element is defined by a single cutting plane or bevel 54 terminating at a tip 52.

FIG. 7 is a schematic cross-sectional diagram of an illustrative piercing element 50 contacting a capsule endcap 26. FIG. 8 is a schematic cross-sectional diagram of an illustrative capsule cavity 24 of an inhaler article 20 with a capsule 25 and piercing element 50.

The orientation of the cutting plane or bevel 54 is illustrated in FIG. 7. The cutting place opposes the central longitudinal axis $L_{CL}$ of the sleeve 40. The central longitudinal axis $L_{CL}$ of the capsule cavity 24 aligned with and co-incident with the central longitudinal axis $L_{CL}$ of the sleeve 40. The tip 52 first penetrates the capsule hemispherical endcap 26 to form the aperture opening and continues to cut the capsule hemispherical endcap 26 until the entire circumference of the piercing element shaft enters the capsule 25. The portion of the perimeter forming the aperture is closest to the central longitudinal axis $L_{CL}$. A hinge of capsule material forming a portion of the aperture opposes the portion of the perimeter closest to the central longitudinal axis $L_{CL}$.

The piercing element 50 is parallel with and offset from the central longitudinal axis $L_{CL}$ a distance $R_O$. The capsule hemispherical endcap 26 has a radius $R_C$ at the circumference of the capsule 25. The piercing element 50 may contact the capsule hemispherical endcap 26 at a point closer to the circumference radius $R_C$ than the central longitudinal axis $L_{CL}$ as described above.

FIG. 9A is front elevation view of an illustrative capsule 25 endcap with aperture 29 after being pierced by the piercing element described herein. FIG. 9B is front elevation view of another illustrative capsule 25 endcap with aperture 29 after being pierced by the piercing element described herein.

FIG. 10 to FIG. 14 illustrate a first assembly method where the piercing element 50 is inserted into the jig 110 before the inner housing 70 is inserted in the jig 110. FIG. 10 illustrates the piercing element 50 sliding into the jig 110. The piercing element 50 extends from a proximal cutting end 51 along a piercing element longitudinal axis to the piercing element distal end 55. The piercing element cutting plane or bevel 54 defines the piercing element proximal cutting end 51. The piercing element cutting plane or bevel 54 is a single plane extending from the piercing element tip to the cylindrical circumference of the piercing element 50 shaft.

The cutting plane or bevel 54 forms an angle with the piercing element longitudinal axis. This angle is preferably from about 25 degrees to about 35 degrees. The jig 110 includes a jig angled planar surface 115 that mates with the piercing element cutting plane or bevel 54. The jig angled planar surface 115 forms an angle that is equal and opposite of the cutting plane or bevel 54 angle.

The jig 110 may include a piercing element aperture 114 that is co-axial with the jig angled planar surface 115. The piercing element 50 may be inserted and rotated (as needed) into the piercing element aperture 114 until the piercing element cutting plane or bevel 54 contacts and mates with the jig angled planar surface 115 as illustrated in FIG. 11, orienting the piercing element 50 for the next steps in assembly.

Then the inner housing 70 may be inserted into the jig 110 as illustrated in FIG. 12 to FIG. 14. The inner housing 70 extends along a longitudinal axis from a proximal end 72 to a distal end 74 an inner housing length. The distal end 74 includes a piercing element aperture 75. The inner housing length mates with a jig opening 112. The jig 110 piercing element aperture 114 is coaxial with jig angled planar surface 115 and the inner housing piercing element aperture 75.

The inner housing 70 slides into the jig 110 until the piercing element 50 distal end 55 is received in the inner housing 70 piercing element aperture 75. Then the piercing element 50 distal end 55 is fixed (as described above) to the inner housing 70, specifically at the piercing element aperture 75. The piercing element cutting plane or bevel 54 is now orientated relative to the inner housing 70 longitudinal axis.

The sub-assembly of the piercing element 50 fixed to the inner housing 70 is then removed from the jig 110 and the remaining elements may then be assembled. For example (see FIG. 2), a spring element 60 distal end is fixed to the inner housing distal end 74 and a sleeve 40 distal end is fixed to the spring element 60 proximal end and forms an inner housing assembly. The sleeve 40 distal end comprising a sleeve closed distal end having a piercing element aperture. The piercing element 50 extending within the spring element 60 and through the sleeve piercing element aperture. The sleeve 40 slides along the inner housing 70 between a first compressed position and a second relaxed position.

This inner housing assembly may be placed into an outer housing 32, as described above to form the inhaler article holder 30.

FIG. 15 to FIG. 21 illustrate a second assembly method where the piercing element 50 is inserted into the jig 110 after the inner housing 70 is inserted in the jig 110.

The jig 110 may be formed of a jig frame 116 and a mating element 111 as shown in FIG. 15. The mating element 111 may be received in a mating aperture 113 in the jig frame 116. The free end of the mating element 111 defines the jig angled planar surface 115 as illustrated in FIG. 16. The jig 110 may include a jig opening 112 configured to mate and receive the inner housing 70.

The second assembly method forms an inner housing assembly 80 (without the piercing element 50) and then inserts this inner housing assembly 80 into the jig 110 as illustrated in FIG. 17 and FIG. 18. The inner housing 70 extends along a longitudinal axis from a proximal end 72 to a distal end 74 an inner housing length.

The inner housing assembly 80 is formed by fixing a spring element 60 distal end to the inner housing 70 distal end 74 and fixing a sleeve 40 distal end to the spring element 60 proximal end. The sleeve 40 distal end including a closed sleeve distal end having a piercing element aperture. The sleeve 40 slides along the inner housing 70 between a first compressed position and a second relaxed position.

The inner housing length mates with a jig opening 112. The jig 110 piercing element aperture 114 is coaxial with jig angled planar surface 115 and the inner housing piercing element aperture 75.

FIG. 19 illustrates inserting the piercing element 50 into the inner housing assembly 80 and into the jig 110. The piercing element 50 may be inserted and rotated (as needed) into the piercing element aperture 114 until the piercing element cutting plane or bevel 54 contacts and mates with the jig angled planar surface 115 as illustrated in FIG. 20 and FIG. 21, orienting the piercing element 50.

The piercing element 50 extends from a proximal cutting end 51 along a piercing element longitudinal axis to the piercing element distal end 55. The piercing element cutting plane or bevel 54 defines the piercing element proximal cutting end 51. The piercing element cutting plane or bevel 54 is a single plane extending from the piercing element tip to the cylindrical circumference of the piercing element 50 shaft.

The cutting plane or bevel 54 forms an angle with the piercing element longitudinal axis. This angle is preferably from about 25 degrees to about 35 degrees. The jig 110 includes a jig angled planar surface 115 that mates with the piercing element cutting plane or bevel 54. The jig angled planar surface 115 forms an angle that is equal and opposite of the cutting plane or bevel 54 angle.

The inner housing 70 distal end 74 includes a piercing element aperture 75. The inner housing length mates with a jig opening 112. The jig 110 piercing element aperture 114 is coaxial with jig angled planar surface 115 and the inner housing piercing element aperture 75.

Then the piercing element 50 distal end 55 is fixed (as described above) to the inner housing 70, specifically at the piercing element aperture 75. The piercing element cutting plane or bevel 54 is now orientated relative to the inner housing 70 longitudinal axis.

The piercing element 50 extends within the spring element 60 and through the sleeve 40 piercing element aperture.

This inner housing assembly may be placed into an outer housing 32, as described above to form the inhaler article holder 30.

For the purpose of the present description and of the appended claims, except where otherwise indicated, all numbers expressing amounts, quantities, percentages, and so forth, are to be understood as being modified in all instances by the term "about." Also, all ranges include the maximum and minimum points disclosed and include any intermediate ranges therein, which may or may not be specifically enumerated herein. In this context, therefore, a number A is understood as A ±2% of A. Within this context, a number A may be considered to include numerical values that are within general standard error for the measurement of the property that the number A modifies. The number A, in some instances as used in the appended claims, may deviate by the percentages enumerated above provided that the amount by which A deviates does not materially affect the basic and novel characteristic(s) of the claimed invention. Also, all ranges include the maximum and minimum points disclosed and include any intermediate ranges therein, which may or may not be specifically enumerated herein.

The invention claimed is:

1. A method of assembling an inhaler article holder having an oriented piercing element, comprising:
    inserting an inner housing into a jig, the inner housing extending along a longitudinal axis and defining an inner housing length from a proximal end to a distal end, the distal end comprising a piercing element aperture, the inner housing length mates with a jig opening, the jig comprising a jig angled planar surface coaxial with the piercing element aperture;
    mating a piercing element cutting plane with the jig angled planar surface, the piercing element extending from a proximal cutting end along a piercing element longitudinal axis to a piercing element distal end, the piercing element cutting plane defines the piercing element proximal cutting end, the piercing element distal end is received in the inner housing piercing element aperture; and
    fixing the piercing element distal end to the inner housing, wherein the piercing element cutting plane is orientated relative to the inner housing longitudinal axis, the piercing element is parallel with but offset from the longitudinal axis of an inhaler device or capsule cavity.

2. The method according to claim 1, further comprising fixing a spring element to the inner housing distal end and fixing a sleeve member to the spring element and forming an inner housing assembly, the sleeve member comprising a sleeve closed distal end having a piercing element aperture, the piercing element extending within the spring element and through the piercing element aperture, the sleeve member slides along the inner housing between a first compressed position and a second relaxed position.

3. The method according to claim 2, wherein the sleeve member extends along a sleeve longitudinal axis from the sleeve closed distal end to a sleeve member open proximal end, the piercing element longitudinal axis is parallel with but offset from the sleeve longitudinal axis.

4. The method according to claim 3 wherein the piercing element cutting plane is orientated facing 180 degrees from the sleeve longitudinal axis.

5. The method according to claim 2, further comprising fixing the inner housing assembly to an outer housing, forming a holder for an inhaler device.

6. The method according to claim 5, wherein the outer housing contains the inner housing assembly and defines an inhaler article opening to receive an inhaler article.

7. The method according to claim 1, wherein the piercing element cutting plane is mated with the with the jig angled planar surface after the inner housing is inserted into the jig.

8. The method according to claim 7, wherein the inner housing is inserted into the jig and the piercing element slides into the inner housing piercing element aperture before the piercing element cutting plane is mated with the with the jig angled planar surface.

9. The method according to claim 8, wherein the inserting step comprises inserting an inner housing comprising a spring element fixed to the inner housing distal end and a sleeve member fixed to the spring element and forming an inner housing assembly, the sleeve member comprising a closed sleeve distal end having a piercing element aperture, the piercing element extending within the spring element and through the piercing element aperture, the sleeve member slides along the inner housing between a first compressed position and a second relaxed position.

10. The method according to claim 7, wherein the inserting step comprises inserting an inner housing comprising a spring element fixed to the inner housing distal end and a sleeve member fixed to the spring element and forming an inner housing assembly, the sleeve member comprising a closed sleeve distal end having a piercing element aperture, the piercing element extending within the spring element and through the piercing element aperture, the sleeve member slides along the inner housing between a first compressed position and a second relaxed position.

11. The method according to claim 1, wherein the piercing element cutting plane is mated with the with the jig angled planar surface before the inner housing is inserted into the jig.

12. The method according to claim 11, wherein the inner housing is inserted into the jig and the piercing element distal end slides into the inner housing piercing element aperture after the piercing element cutting plane is mated with the with the jig angled planar surface.

13. The method according to claim 12, further comprising fixing a spring element to the inner housing distal end and fixing a sleeve member to the spring element and forming an inner housing assembly, the sleeve member comprising a sleeve closed distal end having a piercing element aperture, the piercing element extending within the spring element and through the piercing element aperture, the sleeve member slides along the inner housing between a first compressed position and a second relaxed position.

14. The method according to claim 1, wherein the fixing step comprises fixing the piercing element distal end to the inner housing with an adhesive.

15. The method according to claim 2, wherein the mating step comprises sliding the piercing element into the jig until the piercing element cutting plane contacts the jig angled planar surface and rotating the piercing element until the piercing element cutting plane mates with the jig angled planar surface.

16. The method according to claim 14, wherein the jig comprises a piercing element aperture that is coaxial with jig angled planar surface and the inner housing piercing element aperture.

17. The method according to claim 1, wherein the mating step comprises sliding the piercing element into the jig until the piercing element cutting plane contacts the jig angled planar surface and rotating the piercing element until the piercing element cutting plane mates with the jig angled planar surface.

18. The method according to claim 17, wherein the jig comprises a piercing element aperture that is coaxial with jig angled planar surface and the inner housing piercing element aperture.

19. The method according to claim 1, wherein the jig comprises a piercing element aperture that is coaxial with jig angled planar surface and the inner housing piercing element aperture.

* * * * *